(12) United States Patent  (10) Patent No.: US 7,530,484 B1
Durrani  (45) Date of Patent: *May 12, 2009

(54) SINGLE CARTRIDGE SURGICAL STAPLER

(76) Inventor: Ayaz Mahmud Durrani, 7777 Southwest Freeway, Suite 1068, Houston, TX (US) 77074

( * ) Notice: Subject to any disclaimer, the term of this patent is extended or adjusted under 35 U.S.C. 154(b) by 0 days.

This patent is subject to a terminal disclaimer.

(21) Appl. No.: 12/140,447

(22) Filed: Jun. 17, 2008

Related U.S. Application Data (63) Continuation-in-part of application No. 11/429,781, filed on May 8, 2006, now Pat. No. 7,401,720, which is a continuation-in-part of application No. 10/840,997, filed on May 7, 2004, now abandoned.

(60) Provisional application No. 60/515,635, filed on Oct. 30, 2003.

(51) Int. Cl.
*A61B 17/068* (2006.01)
(52) U.S. Cl. .............. 227/176.1; 227/19; 227/109; 227/175.1; 606/153; 606/219
(58) Field of Classification Search .............. 227/19, 227/176.1, 109, 175.1, 83, 88; 606/153, 606/139, 219, 216
See application file for complete search history.

(56) References Cited

U.S. PATENT DOCUMENTS

| | | | |
|---|---|---|---|
| 2,881,762 A | 4/1959 | Lowrie | |
| 4,534,350 A | 8/1985 | Goldern | |
| 4,595,007 A | 6/1986 | Mericle | |
| 4,617,928 A * | 10/1986 | Alfranca | 227/180.1 |
| 4,979,954 A * | 12/1990 | Gwathmey et al. | 606/219 |
| 5,158,566 A | 10/1992 | Pianetti | |
| 5,163,598 A * | 11/1992 | Peters et al. | 227/176.1 |
| 5,540,374 A * | 7/1996 | Klinzing et al. | 227/176.1 |
| 5,738,474 A | 4/1998 | Blewett | |
| 5,833,698 A * | 11/1998 | Hinchliffe et al. | 606/153 |
| 5,862,972 A * | 1/1999 | Green et al. | 227/175.1 |
| 6,024,748 A * | 2/2000 | Manzo et al. | 606/153 |
| 6,638,297 B1 | 10/2003 | Huitema | |
| 7,223,273 B2 * | 5/2007 | Manzo | 606/153 |
| 7,401,720 B1 * | 7/2008 | Durrani | 227/176.1 |

* cited by examiner

*Primary Examiner*—Scott A. Smith
(74) *Attorney, Agent, or Firm*—Buskop Law Group, PC; Wendy Buskop (57) ABSTRACT

A disposable surgical staple gun that fires two staples in a staggered formation simultaneously to close an incision in the skin without the skin overlapping. The disposable surgical staple gun comprises a frame structure, adapted to be held by a hand with a grip having a handle. A single staple cartridge with an advancing blade and a spring mechanism is adapted for holding staples in a staggered relationship and simultaneously firing two staples in a staggered relationship. A translatable driver manually actuates the single staple cartridge to eject a single pair of staggered staples simultaneously when the disposable surgical staple gun is squeezed. The disposable surgical staple gun additionally includes a spring for returning the translatable driver from a staple ejecting position to a staple reloading position.

12 Claims, 9 Drawing Sheets

SINGLE CARTRIDGE SURGICAL STAPLER

CROSS REFERENCE TO RELATED APPLICATIONS

The present application is a Continuation-in-Part to co-pending U.S. patent application Ser. No. 11/429,781, filed on May 8, 2006, which claims priority to the U.S. patent application Ser. No. 10/840,997, filed on May 7, 2004, now abandoned which in turn claims priority to the Provisional Patent Application Ser. No. 60/515,635, filed on Oct. 30, 2003, the entirety of which are incorporated herein by reference.

FIELD

The present embodiments pertain to a disposable dual surgical stapler gun and more specifically, a dual surgical stapler gun and a method for the use of a dual surgical stapler gun as a tissue fixation device.

BACKGROUND

Conventionally, threaded sutures are used after surgery to close a wound. A suture involves using a plurality of simple stitches, each with a knot, to hold the skin together. There are situations when sutures are unsatisfactory, because the skin overlaps during healing and can cause scarring. Additionally, surgical situations exist where the application of sutures using needle and thread simply take too long. For example, situations in which a patient should not be kept under anesthesia any longer than necessary would require a more rapid method of incision closure. Extended time under anesthesia increases the risk of patient complications.

To provide a fast method to hold skin together, staples were developed having one of three basic shapes: a C-shape, a U-shape, or a circular shaped member. These simple staples have advantages over basic suturing, such as quickness in implementation.

Furthermore, suturing can have a negative effect, in that the skin usually overlaps during healing. Overlapping skin can cause scarring or a ridge to form. The ridge or scar can delay and prolong the healing process, and can also be a cosmetically undesirable feature.

As an alternative to simple suturing, mattress suturing was developed. The mattress suture prevents overlapping of the edges of the incision and improves the healing process by quickening the healing and reducing the incidence of unsightly scarring of the skin.

The mattress suture, regrettably requires an even longer amount of time to implement than a simple suture. The mattress suture causes the wound to heal faster and reduces scarring, but requires a patient to remain under anesthesia for a greater length of time, which can have negative effects. Typically, mattress suturing involves placing a stitch immediately near each edge of an incision, then making a second stitch further from the edge of the incision or wound to approximate the two edges of the incision or wound and reduce tension on the wound while preventing an overlap of the edges of the incision.

The present embodiments were designed to provide the advantages of the mattress suturing technique with the improved quality and efficiency of a staple system.

The surgical staple includes a central portion, which can be straight or slightly curved, with bilateral opposing side portions that are sharply beveled to penetrate the skin easily. This form of staple is generally applied utilizing a stapling apparatus that forcefully drives the opposing beveled side portions through the tissue margins in a ninety degree arc, so that these beveled opposing side portions are generally facing one another at the completion of the stapling operation. The bending of the opposing beveled side portions to form generally parallel planes is often accomplished utilizing a ram and opposing ram plate that cooperatively forcefully bend the opposing beveled side portions during a stapling operation.

Another conventional surgical staple includes a generally U-shaped fastening member having legs that are received in two bores of a receiver member. This type of surgical staple is limited by the need to grasp the members both above and below the tissue plane.

A third type of surgical staple involves an open circular-shaped member, which when closed, has free ends laterally disposed with respect to each other, forming a split-ring configuration.

A need exists to prevent the overlap of the skin when drawing the edges of the skin together. A need exists for a surgical staple gun that is fast to use and will help retain the edges of the skin together for an extended time without an overlap. A need exists during the healing period after surgery for a secure stapling system that holds the skin together without an overlap to provide improved healing and reduced scarring.

The present embodiments have been developed to meet these needs.

SUMMARY

The present embodiments relate to a disposable surgical staple gun that fires two staples simultaneously, in a staggered formation, to close an incision in the skin without the skin overlapping. The simultaneous firing of two staples in a staggered formation provides a closer and stronger approximation of the edges of the incision.

The disposable surgical staple gun includes a frame structure adapted to be held by a hand with a grip having a handle. A single staple cartridge having an advancing blade and a spring mechanism is used to hold staples in a staggered relationship and simultaneously fire two staples in a staggered relationship.

A translatable driver manually actuates the single staple cartridge to eject a single pair of staggered staples simultaneously by the hand. The pair of staggered staples eject simultaneously for engagement on both sides of the incision, forming a mattress suture. The first staple engages a first arm close to a first edge of the incision and a second arm a distance from the second edge of the incision, and the second staple engages a first arm close to a second edge of the wound and the second arm a distance from the first edge of the wound to achieve dual staple mattress suturing.

The disposable surgical staple gun includes a biasing means for returning the translatable driver from a staple ejecting position to a staple reloading position. The translatable driver has a force transmission member linking together the translatable driver and a connecting end portion engageable with a spring connected to the translatable trigger portion.

BRIEF DESCRIPTION OF THE DRAWINGS

The present embodiments will be explained in greater detail with reference to the appended Figures, in which.

The present embodiments are detailed below with reference to the listed Figures.

DETAILED DESCRIPTION OF THE EMBODIMENTS

Before explaining the present embodiments in detail, it is to be understood that the embodiments are not limited to the particular embodiments herein and can be practiced or carried out in various ways.

The present embodiments relate to a disposable surgical staple gun that simultaneously propels two surgical staples in a staggered fashion for closing incisions in skin. In general, the surgical staples have a body portion constructed from a rod and have a planar structure. The body portion consists of a crown with leg projections from each end. Each leg comprises a skin piercing projection to assist in the staple being inserted into the skin.

In a pre-stressed situation, the first width for a surgical staple to be used with humans typically ranges from about 2.5 mm to about 3.5 mm, and the second width typically ranges from about 1.5 mm to about 2.5 mm.

If the surgical staple is designed for use with large animals, such as a horse, cow, giraffe, or other large farm, domestic, or zoo animal, the first width can typically range from about 7.5 mm to about 10.5 mm, and the second width from about 3 mm to about 7.5 mm.

The skin piercing projections are adapted to accept stress, such as from a surgical stapler, such as the Ethicon Proximate RH 35W, or another stapler that is useable to implant surgical staples in the skin of a human or animal. The surgical stapler is used to embed the staple through manual operation, and to transform the generally planar structure of the body of the surgical staple to a stressed position.

In the stressed position, where the piercing projections are disposed on skin on opposite sides of a wound, the piercing projections are bent by the staple into essentially the same plane holding the skin together in a position tantamount to that of a mattress suture.

Upon cessation of the application of stress, the surgical staple maintains the stressed position, enabling the surgical staple to draw opposite margins of skin toward each other in a non-overlapping manner. When the skin piercing projections are bent, the two projections, or arms, are in a 180 degree angular relation to each other. However, it is contemplated that variations from a 180 degree angle would still work, if the variation is no more than 20 degrees.

In an embodiment, the surgical staple is made from a rod of a lightweight, non-rusting alloy, such as stainless steel.

In another embodiment, the surgical staple is adaptable for human use and for small non-human animals. A small non-human animal can include a dog, a cat, a raccoon, a chicken, or similar creatures. For use with small animals, the staple can have a height ranging from about 4 mm to about 6 mm, a length ranging from about 2 cm to about 3 cm, and a diameter ranging from about 0.5 mm to about 0.8 mm.

Alternatively, the novel surgical staple can be used for large non-human animals, such as giraffes, elephants, other zoo animals, horses, cows, large birds, dolphins, or similar large animals that have a skin or skin like covering. In this larger embodiment, the surgical staple can have a height ranging from about 12 mm to about 18 mm, a length ranging from about 6 cm to about 9 cm, and a diameter ranging from about 1.5 mm to about 2.4 mm.

The body of the staple can be a solid rod structure or a hollow, bendable rod.

Figure 1:
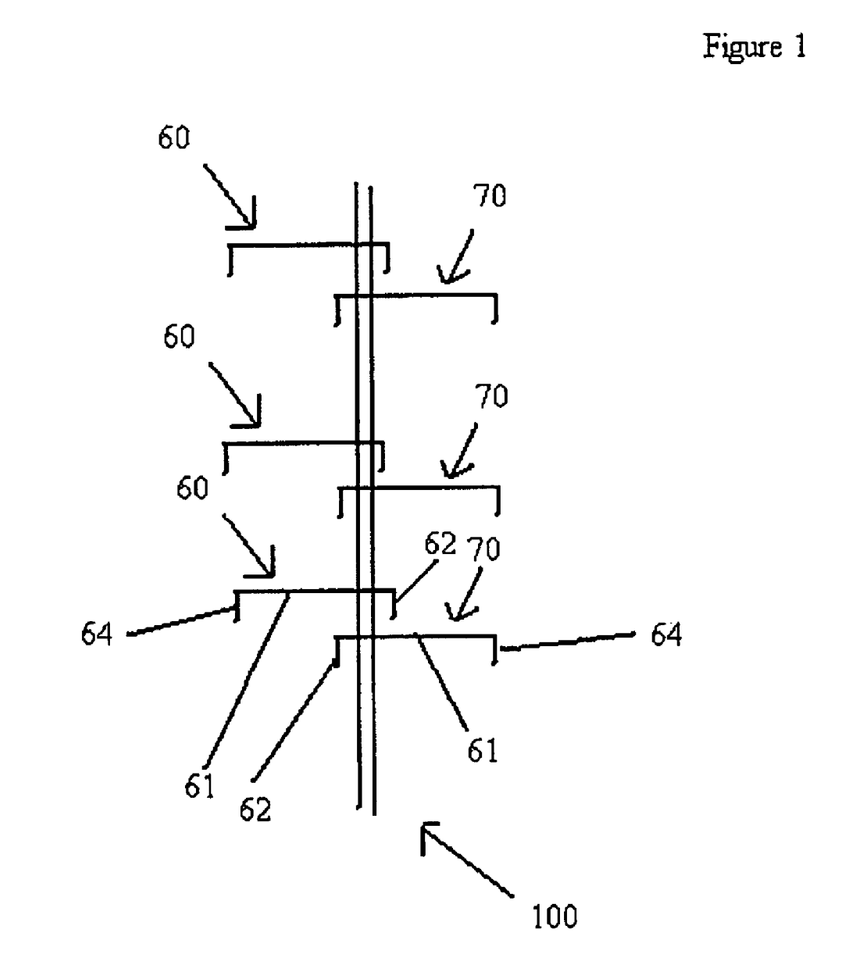
FIG. 1 depicts a dual staple system.

With reference to the figures, FIG. 1 depicts an embodiment of a dual staple system embedded in skin, closing an incision (100). The dual surgical staple system includes repeated use of two staples in a staggered formation, a first staple (60) and a second staple (70), disposed at each staple location. Each staple (60 and 70) includes a crown (61) with two ends. Each staple includes a first arm (62) and a second arm (64) attached at each end of the crown (61). The arms extend from the crown in a direction substantially perpendicular to the crown when the staple is in an unstressed position.

The dual staple system can be used by loading at least two staples into a surgical stapler. The surgical stapler is then located over an incision in the skin that needs to be closed. The stapler is activated, and the arms of each staple are inserted into the skin.

Figure 2:
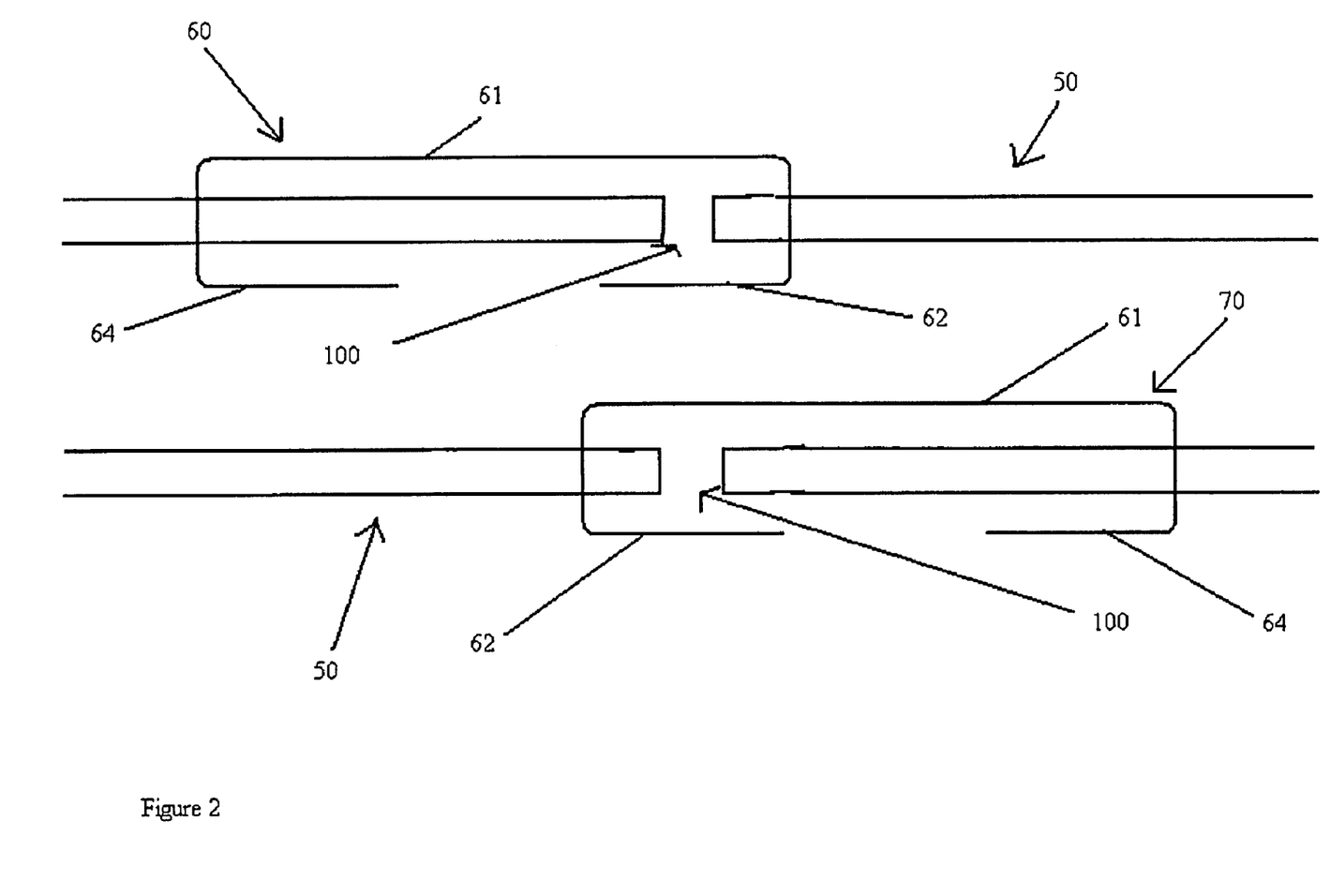
FIG. 2 depicts insertion of the dual staples around an incision.

As depicted in FIG. 2, the first arm (62) of each staple is inserted in the skin (50) near the incision (100) and is bent towards the incision (100). Typically, the first arms (62) intersect the incision in order to ensure that the two sides of the skin are held together. In the depicted embodiment, the first arms (62) are each bent so that the bent ends are close to the surface of the skin. The dual staples, when bent into the skin around the incision, generally can form a rectangular shape or an inverted G-shape with a gap.

The second arm (64) of each staple is inserted in the skin (50) away from the incision (100) and is bent towards the incision (100) to secure stabilization of the union of the two edges of skin.

The disposable surgical staple gun causes no skin overlap, promotes faster healing of the skin, and closes incisions in the skin rapidly using staples, reducing the amount of time required for a patient to be subjected to anesthesia, which can be a lifesaving step. Often, prolonged exposure to anesthesia cannot be tolerated by sick patients.

In another embodiment, each arm can have skin piercing projections for facilitating easier insertion into the skin. The skin piercing projections can include a pointed projection, a chiseled projection, a skewed projection, or combinations thereof.

Medical needles use a "beveled" or chisel-like structure to provide a means to invade the skin with maximum ease and minimal pain. In another embodiment, each of the skin piercing projections can have a beveled end.

In another embodiment of the surgical staple, the pre-stressed surgical staple is placed upon the skin, and then the staple is stressed, drawing the skin piercing projections slightly together, with the first and second skin piercing projections becoming disposed in a generally horizontal plane relative to the body of the staple.

The mattress staple can be used with all surgical skin incisions.

The present embodiments also relate to a disposable surgical staple surgical gun, that fires two staples simultaneously, from a single staple cartridge, in a staggered formation, to close an incision in the skin without the skin overlapping.

The disposable surgical staple gun has a frame structure, adapted to be held by a hand with a grip having a handle. The disposable surgical staple gun has a single staple cartridge that has an advancing blade and a spring mechanism. The single staple cartridge is adapted for holding staples in a staggered relationship, and for firing two staples simultaneously in a staggered relationship.

A translatable driver can be positioned on the disposable surgical staple gun for manually actuating the single staple cartridge to eject a single pair of staples simultaneously by the hand. The pair of staggered staples are ejected simultaneously for engagement on either side of an incision, forming a mattress suture. The first staple engages a first arm close to a first edge of the incision and a second arm a distance from a second edge of the incision, and the second staple engages a first arm close to a second edge of the incision and a second arm a distance from the first edge of the incision to achieve dual staple mattress suturing.

The disposable surgical staple gun additionally includes a biasing means for returning the translatable driver from a staple ejecting position to a staple reloading position. The translatable driver can include a force transmission member linking together the translatable driver and a connecting end portion engageable with a spring connected to the translatable trigger portion.

In an alternate embodiment the disposable surgical staple gun can include a frame structure comprising a staple track portion inserted into a holder portion.

In another embodiment, the single staple cartridge can include two staple tracks, disposed in a staggered relationship, which can be disposed atop one another, side-by-side, back to back, or in another staggered adjacent relationship.

In yet another embodiment, the disposable surgical staple gun fires at least two staples simultaneously each time it is fired. After firing, the two staples are staggered in a position from each other across the incision.

In still another embodiment, the disposable surgical staple gun uses staples that have a skin piercing projection that can include a point projection, a chiseled projection, a skewed projection, or combinations thereof. The staples can include a lightweight, non-rusting alloy of a metal. Each staple can have:

a. a height ranging from about 4 mm to about 6 mm;

b. a length ranging from about 2 cm to about 3 cm; and c. a diameter ranging from about 0.5 mm to about 0.8 mm.

In another embodiment, the disposable surgical staple gun can be formed from a crystalline polymer, or a metal. The gun can have a first width ranging from about 2.5 mm to about 3.5 mm and a second width ranging from about 1.5 mm to about 2.5 mm.

The present embodiments also relate to a method for surgically stapling an incision using the simultaneous injection of a staggered pair of surgical staples. The steps begin by inserting surgical staples into a disposable surgical staple gun.

The surgical staples each have a crown with two ends, a first arm, and a second arm. The arms of the staple include a skin piercing projection and extend from the crown in a direction substantially perpendicular to the crown when the staple is in its initial shape.

The disposable surgical staple gun fires two staples simultaneously, in a staggered relation to one another, to close an incision in the skin without the skin overlapping.

The next step for surgically stapling the incision includes placing the disposable surgical staple gun over the incision and activating the stapler by squeezing the grip to simultaneously insert at least two staples from a single staple cartridge into the skin.

By activating the stapler, the first arm of each staple engages the skin nearest the incision on opposite sides of the incision. The crowns of each staple are to be located adjacent and parallel to one another, and the second arm of each staple engage the skin away from the incision on opposite sides of the incision. The disposable surgical staple gun then bends each arm of the staples, forming an inverted G-shape with a gap.

In an embodiment, the disposable surgical staple gun bends each arm to ensure that the first arm of each staple intersects the incision.

In yet another embodiment, the disposable surgical staple gun bends each arm, thereby closing the incision in the skin without the skin overlapping.

Figure 3:
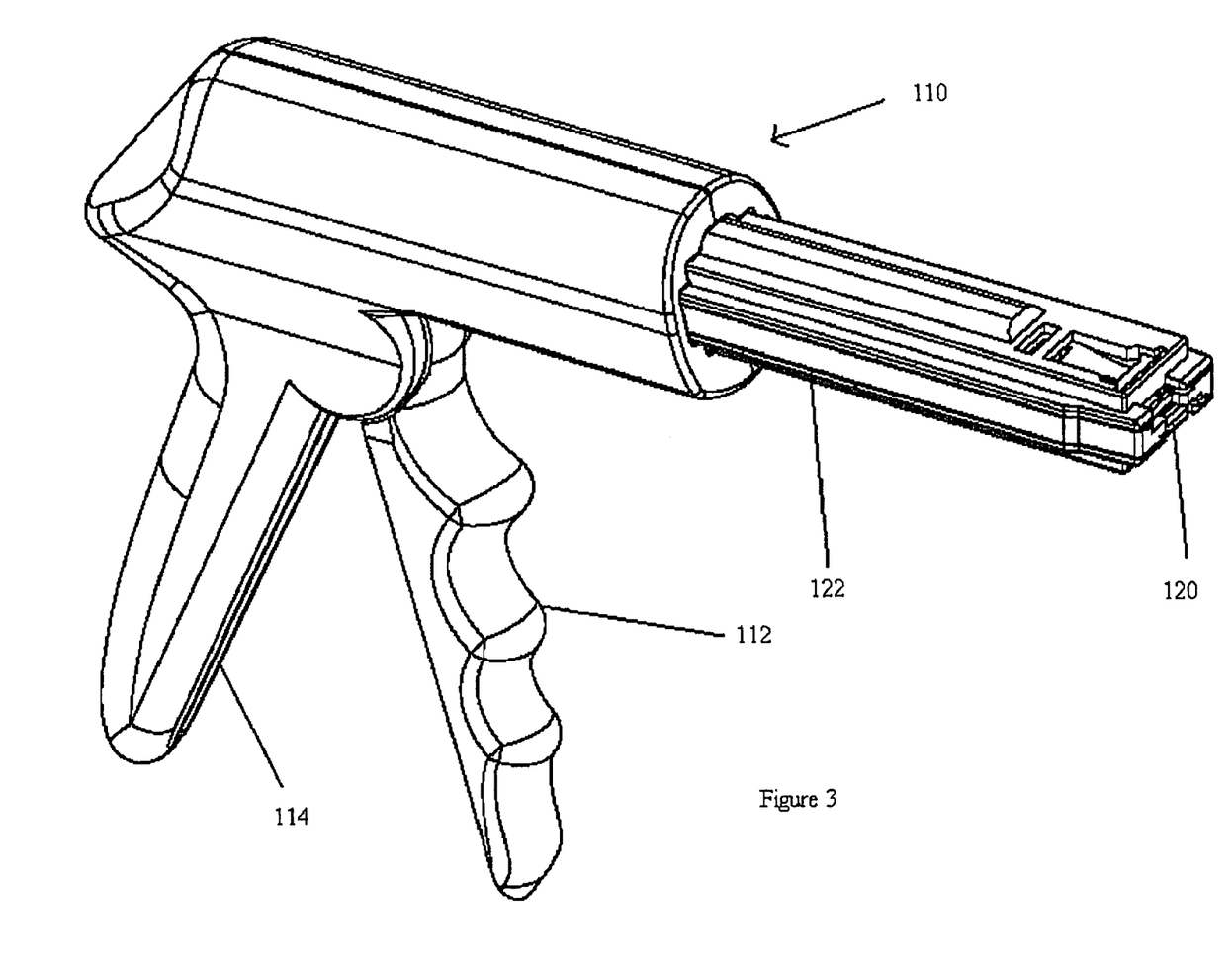
FIG. 3 depicts a perspective view of an embodiment of a disposable surgical staple gun.

FIG. 3 depicts a perspective view of the disposable surgical staple gun. The disposable surgical staple gun (110) has a grip (112) with a handle (114). A single staple cartridge (120) is located in the on the disposable surgical staple gun. The single staple cartridge (120) extends throughout the disposable surgical staple gun, as shown, through the staple track portion (122).

Figure 4:
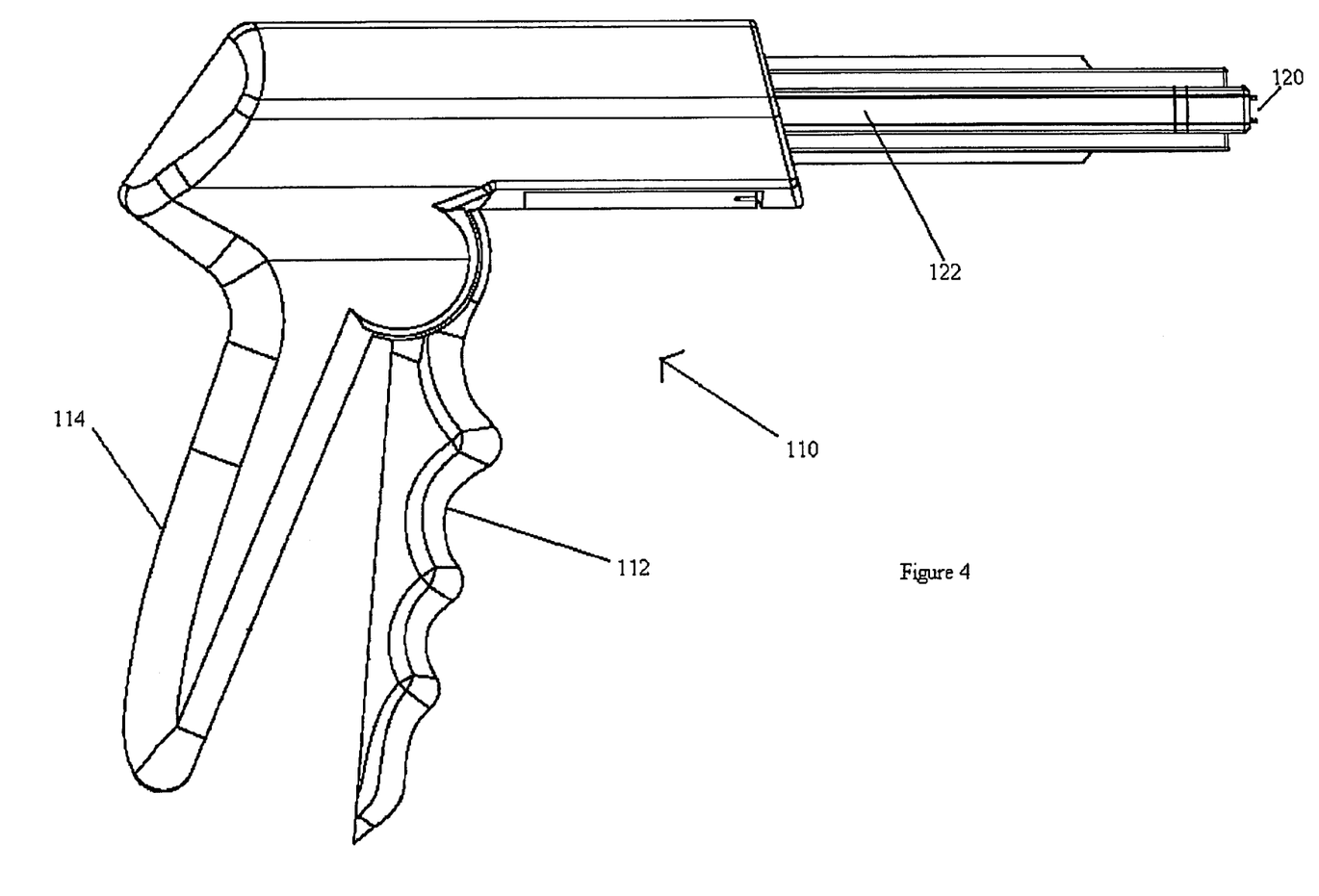
FIG. 4 depicts a side view of the disposable surgical staple gun.

FIG. 4 depicts a side view of the disposable surgical staple gun (110) with the grip (112) compressed. When the grip is compressed staples are ejected from the holes in the front of the disposable surgical staple gun.

Figure 5:
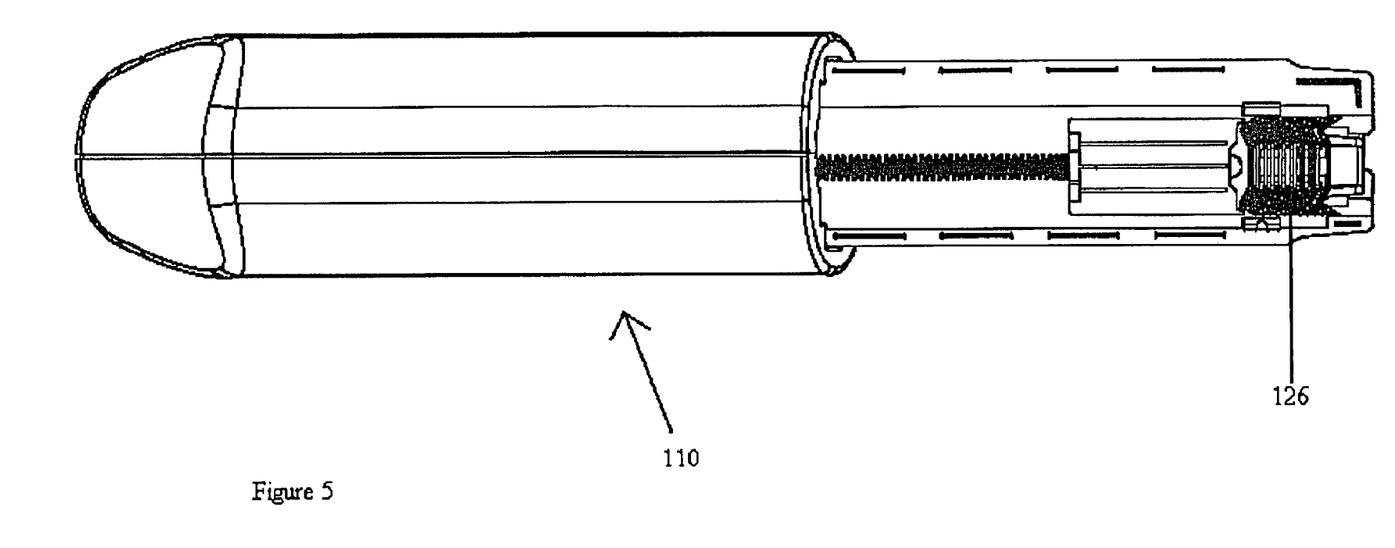
FIG. 5 depicts a top view of the disposable surgical staple gun.

FIG. 5 depicts a top view of the disposable surgical staple gun (110). From the top view, staples (126) within the single staple cartridge are depicted ready to be manually actuated by the translatable driver.

Figure 6:
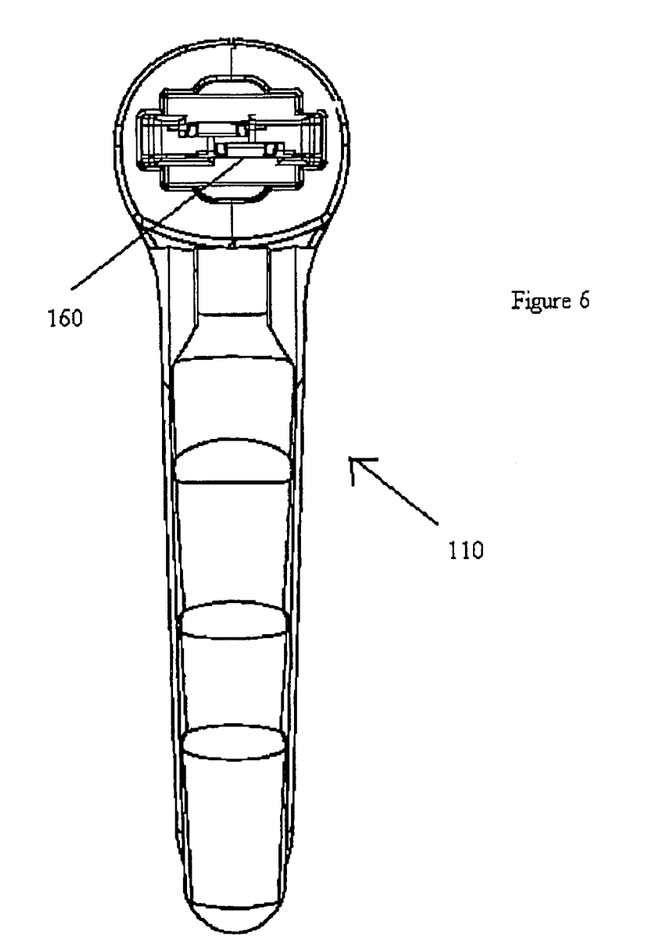
FIG. 6 depicts a front end view of the disposable surgical staple gun.

FIG. 6 depicts a front view of the disposable surgical staple gun (110). The hole(s) from which the staples are ejected (160) eject the staples in a staggered arrangement, as shown in FIG. 2.

Figure 7:
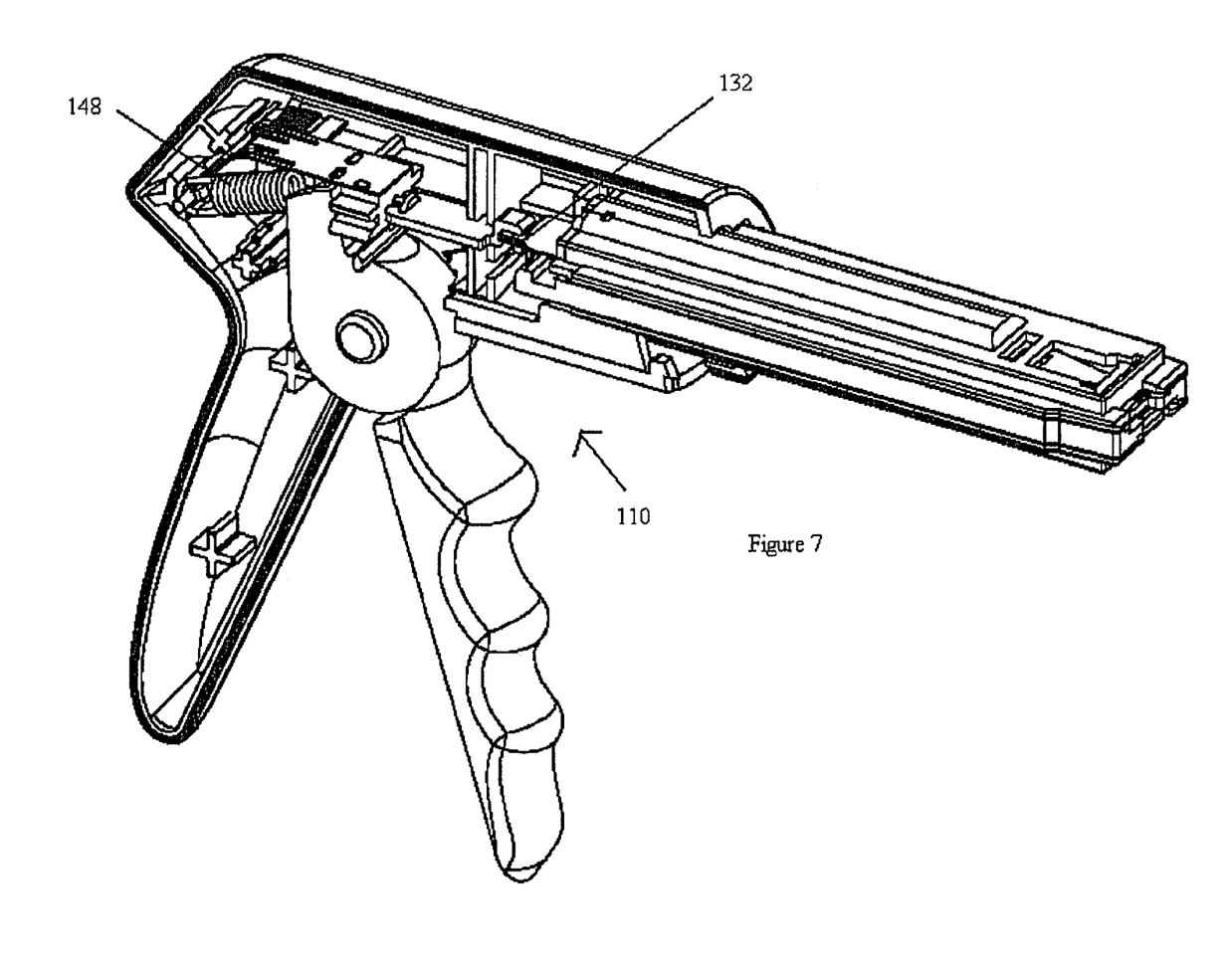
FIG. 7 depicts an open perspective view of the disposable surgical staple gun.

FIG. 7 is a open perspective view of the disposable surgical staple gun (110). A translatable driver (132) is used for manually actuating the single staple cartridge to eject a single pair of staples by hand. A biasing means (148) is used to return the translatable driver from a staple ejecting position to a staple reloading position.

Figure 8:
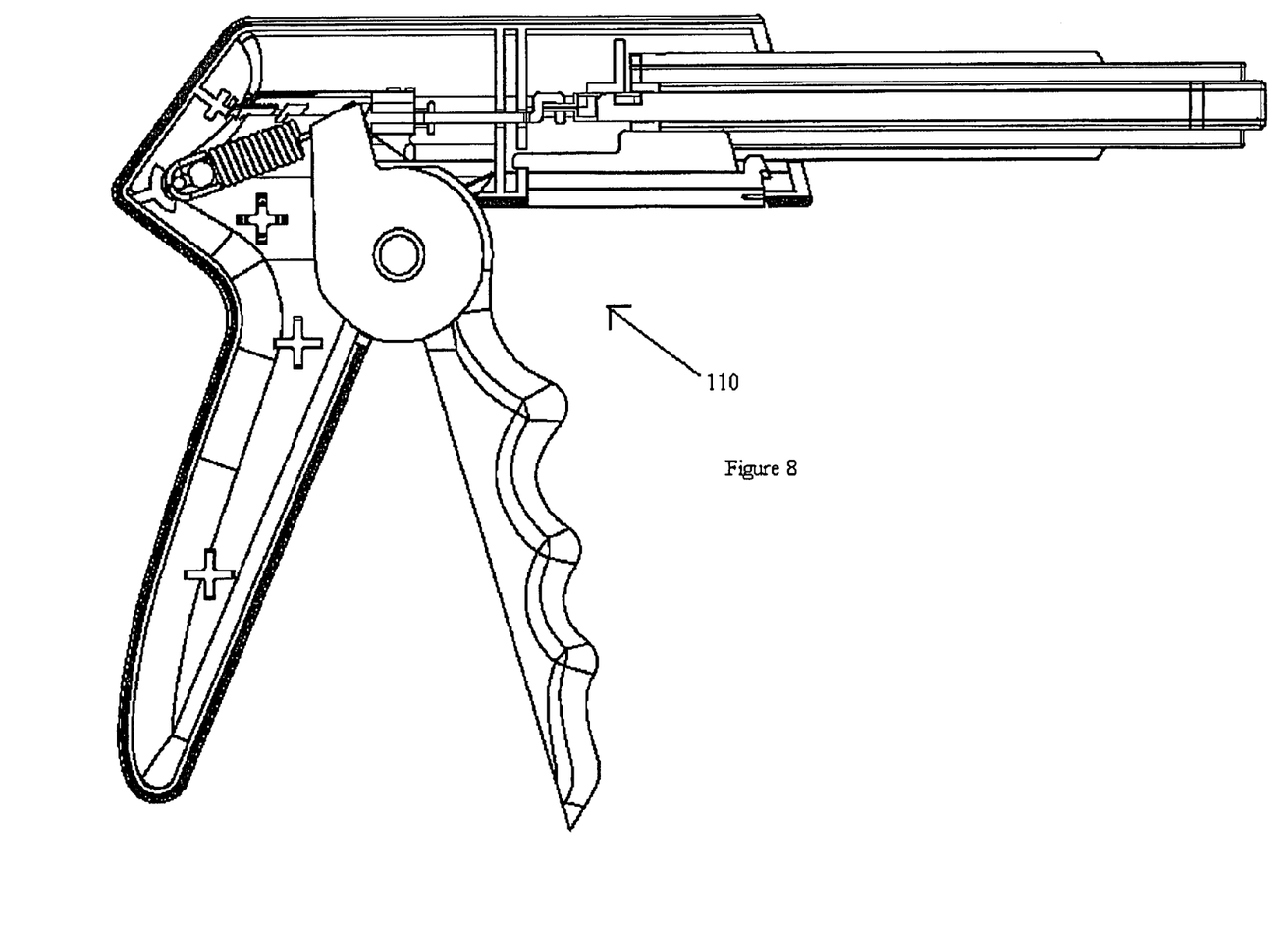
FIG. 8 depicts an open side view of the disposable surgical staple gun.

FIG. 8 is a open side view of the disposable surgical staple gun (1110).

Figure 9:
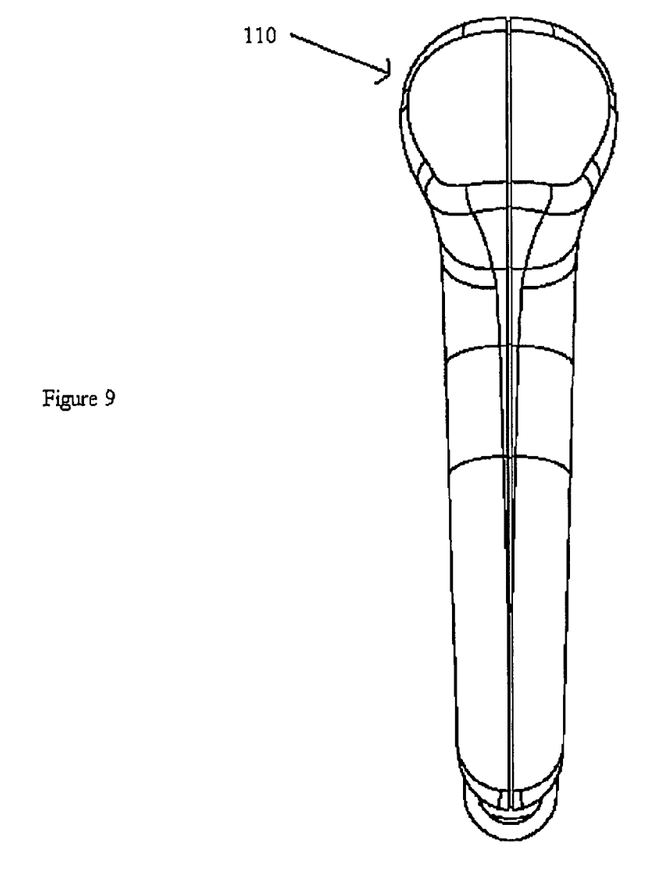
FIG. 9 depicts a back end view of the disposable surgical staple gun.

FIG. 9 is a back end view of the disposable surgical staple gun (1110).

While the embodiments have been described, it should be understood that within the scope of the appended claims the embodiments might be practiced or carried out in other ways than as specifically described herein.

What is claimed is:

1. A disposable surgical staple gun for firing two staples in a staggered formation simultaneously to close an incision in the skin without the skin overlapping, the disposable surgical staple gun comprising:
   a. a frame structure adapted to be held by a hand with a grip having a handle;
   b. a single staple cartridge comprising an advancing blade and a spring mechanism, wherein the single staple cartridge is adapted for holding staples in a staggered relationship and simultaneously firing two staples in a staggered relationship;

c. a translatable driver for manually actuating the single staple cartridge to eject a single pair of staggered staples simultaneously by the hand, wherein the single pair of staggered staples are ejected simultaneously for engagement on either side of the incision, forming a mattress suture, and wherein the first staple engages a first arm close to a first edge of the incision and a second arm a distance from a second edge of the incision and the second staple engages a first arm close to a second edge of the wound and the second arm a distance from the first edge of the incision to achieve dual staple mattress suturing; and d. biasing means for returning the translatable driver from a staple ejecting position to a staple reloading position, wherein the translatable driver has a force transmission member linking together the translatable driver and a connecting end portion engageable with a spring connected to the translatable trigger portion.

2. The disposable surgical staple gun of claim 1, wherein the frame structure comprises a staple track portion inserted into a holder portion.

3. The disposable surgical staple gun of claim 1, wherein the single staple cartridge comprises a first staple track and a second staple track disposed in a staggered relation to the first staple track.

4. The disposable surgical staple gun of claim 1, wherein the disposable surgical staple gun uses staples that have a skin piercing projection comprising a point projection, a chiseled projection, a skewed projection, or combinations thereof.

5. The disposable surgical staple gun of claim 1, wherein the staples comprise a lightweight, non-rusting alloy of a metal.

6. The disposable surgical staple gun of claim 1, wherein the disposable surgical staple gun is formed from a crystalline polymer, a metal, or combinations thereof.

7. The disposable surgical staple gun of claim 1, wherein the staples each comprise:
 a. a height ranging from about 4 mm to about 6 mm;
 b. a length ranging from about 2 cm to about 3 cm; and
 c. a diameter ranging from about 0.5 mm to about 0.8 mm.

8. The disposable surgical staple gun of claim 1, wherein the disposable surgical staple gun fires at least two staples simultaneously each time it is fired.

9. The disposable surgical staple gun of claim 8, wherein the at least two staples are fired in a staggered in position from each other across the incision.

10. A method for surgically stapling an incision using the simultaneous ejection of offset twin surgical staples comprising the steps of:
 a. inserting surgical staples into a disposable surgical staple gun;
 b. wherein the surgical staples each comprise:
  (a) a crown comprising two ends, a first arm, and a second arm attached at each end of the crown, wherein the arms comprise a skin piercing projection, wherein the arms extend from the crown in a direction substantially perpendicular to the crown when the staple is in its initial shape; and
  (b) wherein the disposable surgical staple gun fires two staples simultaneously to close an incision in the skin without the skin overlapping;
 c. placing the disposable surgical staple gun over the incision;
 d. activating the stapler by squeezing a grip to simultaneously insert at least two staggered staples from a single staple cartridge into the skin, enabling:
  (a) the first arm of each staple to engage the skin nearest the incision on opposite sides of the incision;
  (b) the crowns of each staple to be located adjacent and parallel to one another; and
  (c) the second arm of each staple to engage the skin away from the incision on opposite sides of the incision;
 e. using the disposable surgical staple gun to bend each arm on the staples forming an inverted G-shape with a gap.

11. The method of claim 10, wherein the step of using the disposable surgical staple gun bends each arm to ensure that the first arms intersects the incision.

12. The method of claim 10, wherein the step of using the disposable surgical staple gun bends each arm thereby closing the incision in the skin without the skin overlapping.

* * * * *